United States Patent [19]

Lynch

[11] Patent Number: 5,306,303
[45] Date of Patent: Apr. 26, 1994

[54] BONE INDUCTION METHOD

[75] Inventor: Kenneth L. Lynch, Brookfield, Wis.

[73] Assignee: The Medical College of Wisconsin, Inc., Milwaukee, Wis.

[21] Appl. No.: 794,747

[22] Filed: Nov. 19, 1991

[51] Int. Cl.$^5$ ............................ A61F 2/28; A61F 2/02
[52] U.S. Cl. ........................................ 623/16; 623/66; 623/11
[58] Field of Search ...................... 623/11, 13, 15, 16, 623/17, 18, 66

[56] References Cited

U.S. PATENT DOCUMENTS

| | | | |
|---|---|---|---|
| 4,629,464 | 12/1986 | Takata et al. | 623/16 |
| 4,654,314 | 3/1987 | Takagi et al. | 623/16 |
| 4,780,450 | 10/1988 | Sauk et al. | 623/16 |
| 4,794,046 | 12/1988 | Nagai | 623/16 |
| 4,795,467 | 1/1989 | Piez et al. | 623/16 |
| 4,932,973 | 6/1990 | Gendler | 623/16 |

OTHER PUBLICATIONS

Lynch et al., "Osteoinductivity by Subcutaneous Implantation of a Collagen/Ceramic Composite," 3rd International Symposium on Ceramics in Medicine, Abstracts (Nov. 18-20, 1990).
Bucholz et al., The Orthopedic Clinics of North America, vol. 18, No. 2, pp. 323-334 (Apr. 1987).
Ohgushi, Clinical Implant Materials, vol. 9, Elsevier Science Publishers (1990), pp. 225-230.
Ohgushi et al. Journal of Orthopaedic Research, 7:568-578 (1989).
"Osteoinductivity by Subcutaneous Implantation of a Fibrillar Collagen and Calcium Phosphate Ceramic Composite", Lynch et al., pp. 295-304, Bioceramics, vol. 3, Apr. 1992.
"Biologic Principles of Bone Induction," A. H. Reddi et al., pp. 207-212, Bone Grafting, Orthopedic Clinics of North America, vol. 18, No. 2, Apr. 1987.
"Bona Fide Osteoinductive Factors," A. H. Reddi et al., The Journal of NIH Research, vol. 2 pp. 67-70, May 1990.
Pp. 692-703, The Journal of Bone and Joint Surgery, Incorporated, vol. 73A, No. 5, Jun. 1991.
"Composite Grafts of Human Bone Marrow Cells and Porous Ceramics," Ohgushi et al., pp. 279-285, Bioceramics, vol. 3, Nov. 20, 1992.

Primary Examiner—David Isabella
Attorney, Agent, or Firm—Quarles & Brady

[57] ABSTRACT

A method of inducing bone growth in a living animal consists of implanting in the soft tissue or bone of the animal a bone morphogenetic protein-free, ceramic consisting of a calcium phosphate which is at least partially resorbable, and leaving the ceramic in place until new bone growth is induced.

5 Claims, No Drawings

BONE INDUCTION METHOD

FIELD OF THE INVENTION

The present invention relates to bone induction. More particularly, it relates to a method of inducing new bone growth using a calcium phosphate ceramic.

BACKGROUND OF THE INVENTION

It is known that osteogenin and other bone morphogenic proteins when implanted into the soft tissue of an animal, such as a rabbit, a rat or a dog, induce the formation of new bone. Such compounds are considered osteoinductive. It also is known that ceramics, especially calcium hydroxyapatite and other calcium phosphates and mixtures thereof, are osteoconductive (i.e., when placed next to viable bone they provide a framework for the rapid incorporation of connective tissue and subsequent bone ingrowth).

The ceramics are inorganic and do not normally cause an immunological reaction. However, the bone morphogenic proteins may cause an undesirable immunological response.

It obviously would be desirable to have a method of inducing bone growth in animals, including humans, without using bone morphogenic proteins that might cause an undesirable immunologic response in the animals.

SUMMARY OF THE PRESENT INVENTION

It is an object of the present invention to disclose a method of inducing the growth of bone in a living animal without using bone morphogenic proteins.

It also is an object to disclose novel compositions which are free of bone morphogenic proteins and which nevertheless induce bone growth when implanted into living animals.

We have made the discovery that new bone growth can be induced in a living host animal by implanting into the soft tissue or bone of said animal an implant comprising a safe and effective amount of a bone morphogenic protein-free porous ceramic consisting of a calcium phosphate material which is at least partially resorbable, sustaining said animal and leaving said implant in place until the host tissue responds by causing angiogenesis (the development of blood vascular supply), multinucleate giant cell resorption of some of the ceramic and the replacement of some of the ceramic with intramembranous bone formed by an endosteal membrane which produces active osteogenic osteoblasts characteristic of new bone. A favorable osteogenic host tissue response usually can be seen to be starting after about seven weeks.

This discovery is truly unexpected because the prior art consistently and expressly states that ceramics that do not contain bone morphogenetic proteins are osteoconductive and not osteoinductive (Buckholz et al Orthopedic Clinics of North America, Vol. 18, No. 2, pp. 323–334 (April 1987).

The preferred porous ceramic composite which is employed in the method of the present invention may contain from about 10% to about 90% by weight of hydroxyapatite and about 90% to about 10% by weight of a resorbable calcium phosphate. Especially preferred are granules or blocks of a sintered ceramic comprised of 60% hydroxyapatite and 40% $\beta$-tricalcium phosphate, having a mean pore size of about 300 to about 700 $\mu$m, which is described in the Ohguski et al. article, titled "Marrow Cell Induced Osteogenesis and Chondrogenesis in Porous Calcium Phosphate Ceramics" which appeared in Clinical Implant Materials Vol. 9, Elsevier Science Publishers (1990) p. 225–230.

We also have discovered that implants which have more intricate and fragile shapes than granules and blocks can be conveniently formed from novel ceramic compositions which also contain a mucopolysaccharide binder.

These and other objects and advantages will be apparent to those skilled in the art from the description and experimental work contained hereinafter.

DESCRIPTION OF THE PREFERRED EMBODIMENT

In the preferred practice of the method of the present invention the implant which is implanted is either a block or granules of a porous ceramic composite of hydroxyapatite and $\beta$-tricalcium phosphate in 60/40 ratio (range 65/35±15% each). This porous composite, which contains no osteoinductive proteins, is found to induce de novo bone formation when it is implanted into subcutaneous or intramuscular sites; and the animal is kept alive and the implant is kept in place until the host tissue cells respond to the ceramic implant by causing angiogenesis (blood vascular supply), multinucleate giant cell resorption of ceramic, and replacement of the ceramic with intramembranous bone formed by an endosteal membrane which produces active osteogenic osteoblasts. This usually starts to occur after about seven to nine weeks in the canine subcutaneous tissue, for example.

It appears that the implanted ceramic provides an appositional supportive interface for tissue attachment initially and that resorbable calcium phosphate is then simultaneously and progressively removed by giant cells. The early bone formed is fine cancellous woven bone which rapidly becomes dense, compact cancellous bone (convoluted primary vascular bone) of plexiform structure. Many of the ceramic resorption cavities are lined by bone, and normal bone marrow cells also develop with red and white cell lines and megakaryocytes. The new bone thus formed becomes hematopoietic.

Clinical uses for the method and compositions of the present invention include:

1. Applications where autogenous bone graft normally would be used, but an insufficient amount is available. The ceramic may be used alone or as a supplement to avoid the use of allograft or bone from "banks" to prevent disease transmission.

2. For the bridging of large tumor cavities after removal of tumor.

3. The formation of custom-sized or custom-shaped blocks or sheets for cranial, maxillofacial reconstructive bone replacement and remodeling.

4. For plastic reconstructive surgery to assist new bone formation at sites where necessary.

5. For augmentation with metal or polymer instrumentation in stress-bearing locations for biological fixation in skeletal repair. (It does not have initial structural strength suitable for use as a stress-bearing material. After growth, the strength is equal to bone.)

6. For spinal intervertebral joint fusions (disk arthroplasty).

7. For any procedure requiring arthrodesis (all joint fusions).

8. For the replacement of necrotic bone segments in foot or hand (e.g. ischemic necrosis of navicular or talus).

9. For the replacement of contents of femoral or humeral head following decompression and excochleation by curettage, to become a new center of ossification.

10. For the bridging of segmental defects in delayed union or non-union of fractures.

11. For surgical reattachment of avulsed bone fragments.

12. For the stimulation of stem cells in hemopoietic function of normal cancellous bone marrow by implants in S.C. sites in humans.

13. For preparing animal model of implants for the study of the basic science fundamental to the developmental biology of intramembranous bone and primary vascular bone in skeletal development.

14. For animal models for the study of hematopoiesis in mammals.

The foregoing and additional uses of the method and composition of the present invention will be apparent to those skilled in the art. The practice of the invention is further illustrated by the description of the Experimental Work which was conducted.

Experimental Work

Introduction: It has been shown that ceramics comprised of Hydroxyapatite (HA) and Tricalcium Phosphate (TCP) are osteoconductive and may be useful as bone graft substitutes. We previously investigated a ceramic composite containing both crystalline forms of these materials as an osteoconductive material. In the Experimental Work described hereinafter the osteoinductive properties of such composites are demonstrated.

Materials and Methods: Porous granules of 60% HA and 40% $\beta$-TCP of 0.5 to 1.0 mm. diameter in size were mixed with Type I bovine dermal collagen to form lyophilized implants. Via a midsagittal incision in the dorsal skin of the dog under general anesthesia, the implants were sewn into subcutaneous pockets. Control implants of the ceramic which did not contain the collagen were also implanted. Implants were then removed at 1,2,3,5,7,9 and 11 weeks and at 3,4,6 and 9 months. One half of each specimen was decalcified and sectioned at 5 $\mu$m. Adjacent sections were stained with H & E for morphology and Safranin-O/Fast Green to identify cartilage. The other half was left undecalcified, embedded in glycolmethacrylate, sectioned to 200 $\mu$m., and microradiographed.

Results: At one week, histiocyte and fibroblast proliferation was seen around the ceramic residue with occasional monocytes and lymphocytes. In addition, a few polymorphonuclear (PMN) cells were seen in the collagen binder. At the periphery of the ceramic granules, a few multi-nucleated giant (MNG) cells were noted. At two weeks the acute inflammation subsided as manifested by a decrease in PMN cells. The round cells and histiocyte infiltration remained the same. There was an increase in vascular and fibroblast proliferation. MNG cells were increased. Greater hemorrhage appeared, probably related to the vascular proliferation. At three weeks the inflammatory round cell reaction and histiocyte infiltration remained. Fibrous tissue and blood vessels grew into the ceramic material. At the fifth week inflammation had subsided. Further ingrowth of fibrous tissue into the ceramic material was seen. Many MNGs were found invading the rarified ceramic residue. Changes in the seventh week samples were similar to the fifth week. Ingrowth of fibrous tissue was observed during the ninth week. At this time, calcified woven bone was observed both histologically and microradiographically. Many MNGs were seen resorbing ceramic material. At eleven weeks, there was good bone formation accompanied by receding fibrous tissue. No bone marrow was evident. Osteoblasts were actively forming bone while MNGs were resorbing the ceramic. Control material of dermal fibrillar collagen had disappeared from the implant site at 11 weeks. Normal reticular subdermal tissue was found as replacement healing. At about 11 weeks, the control HA/TCP granules without the collagen were observed to have some bone spicules but the fibrous tissue infiltrate predominated. At three months bone with haversian systems was seen microradiographically, with both the ceramics with collagen and without. At four months bone marrow was observed in both types of implants with full red and white cell lines. Megakaryocytes were found. At six and nine months, with both types of implants bone maturation and marrow cell formation was progressive at the expense of the disappearing ceramic resorbed by giant cells. The new bone continued to consolidate as compact cancellous lamellar bone.

Discussion/Conclusions: The following conclusions could be made: 1) Both the implants with Type 1 collagen and HA/TCP ceramic and the HA/TCP ceramic without collagen were osteoinductive. 2) The implants caused a short term chronic inflammatory foregn body type reaction. In addition, it appears that: 3) The biphasic nature of this ceramic provides a soluble phase ($\beta$-TCP) which initiates the giant cell response, is resorbed and may then initiate osteoblast differentiation, and that it provides local calcium phosphate to form calcified woven bone. The remaining hydroxyapatite appears to provide an appositional interface and scaffold for the new bone formation. 4) The mechanism follows a pattern of intramembranous osteogenesis. 5) Collagen appears to serve as an enhancing factor by acting as a bridge for vascular infiltration and a pathway for the development of a new matrix bearing multipotential mesenchymal cells. However, new bone growth was found to occur even when no collagen or other bone morphogenic protein is present if the animal is sustained and the implants are left in place.

In addition to hydroxyapatite and $\beta$-tricalcium phosphate, a variety of other calcium phosphate mineral materials which are at least in part resorbable can be used in the practice of the present invention. As used herein, "calcium phosphate mineral" materials refers to those materials composed of $Ca^{+2}$ and phosphate ions, regardless of the microstructure protonation status of the phosphate, or extent of hydration. Calcium phosphate mineral materials include a variety of forms, such as the commercially available forms of tricalcium phosphate for example. SYNTHOGRAFT® tricalcium phosphate.

The hydroxyapatite may be a commercial hydroxyapatite such as PERIOGRAF®, ALVEOGRAF®, INTERPORE®, ORTHOMATRIX™ HA-1000™, or ORTHOMATRIX™ HA-500™ hydroxyapatite particulate preparations.

The hydroxyapatite and other tricalcium phosphates may be prepared by synthetic methods. While the mineral content of bone could be harvested and purified for this purpose, more economically prepared and controlled compositions are preferable, both as a matter of cost and of quality. Preferred granule sizes are in the range of 100–2000μ. If solid blocks are desired, these are prepared from powders which can be compacted, sintered, and/or calcined. The implants may be prepared simply by mixing the two components into a cohesive mass and then loading the mixture into an appropriate container which is packaged to supply a "wet" product that can be shaped by the user. Alternatively, the mixture can be cast into a desired shape (e.g., blocks, squares, sheets) and then lyophilized or air dried and packaged to provide a "dry" product. The degree of dryness obtained is, of course, arbitrary, since both "wet" and "dry" forms are usable. However, as used herein, the "dry" form refers to mixtures containing <1.0% moisture. For lyophilized material, substantially all moisture is removed by freeze-drying. The dry material is rigid and can be cut with a sharp instrument. Blocks may be made from the granular form by compacting in the presence of liquid or a binder and then drying. The preferred block is a composite of a sintered ceramic containing 60% hydroxyapatite and 40% β-tricalcium phosphate having a mean pore size of about 300 to about 700 μm. When more malleable shapes are required the composite also contains an effective amount of a binder.

Representative of the binders that can be used are mucopolysaccharide binders, such as mucin, and chrondroitin sulfate. Mucin is preferred because it is autoclavable. If mucin is used implants can be formed in the desirable shape and size by simple compression molding. In addition, the mucopolysaccharides do not normally produce an immunologic response.

The implants can be used as previously indicated to augment bone and fill bony defects, for example, periodontal bony pockets, tooth extraction sockets, and jaw cysts. An important use includes alveolar ridge augmentation. The procedures for the surgical implantation are known in the art. For alveolar ridge augmentation, the implant is inserted under the periosteum in places where augmentation is desired. In orthopedic and reconstructive applications, mineral in the form of porous blocks may also be indicated, particularly where the graft must bear stress. Implantation of the blocks is effected by standard surgical techniques.

It will be apparent to those skilled in the art that a number of modifications and changes may be made without departing from the spirit and scope of the invention. For example, the method of the present invention may also be used where the need is for functioning bone marrow and not bone per se. Therefore, it is intended that the invention only be limited by the claims.

I claim:

1. A method of inducing new bone growth in an animal which comprises: implanting in the soft tissue of said animal a porous bone-inducing ceramic implant free of bone morphogenetic proteins and bone-marrow cells consisting essentially of a calcium phosphate which is at least partially resorbable; sustaining said animal; and, leaving the implant in place until the host tissue responds to the implant by causing angiogenesis, multinucleate giant cell resorption of some of the calcium phosphate and the replacement of the ceramic with intramembranous bone formed by an endosteal membrane which produces active osteogenic osteoblasts which are characteristic of new bone.

2. A method of claim 1 in which the ceramic implant is a block of a sintered crystalline mixture of hydroxyapatite and βtricalcium phosphate.

3. A method of claim 1 in which the calcium phosphate is selected from calcium hydroxyapatite, β-tricalcium phosphate and mixtures thereof.

4. A method of claim 1 in which the implant includes a mucopolysaccharide and mucoprotein binder.

5. A method of growing new bone marrow in a living animal which comprises: implanting into the soft tissue of said animal a bone morphogenetic protein-free and cell free, porous implant consisting essentially of a calcium phosphate which is at least partially resorbable; and leaving said implant in place; and sustaining said animal until new bone marrow is formed.

* * * * *